US006839583B1

(12) United States Patent
Lewandowski et al.

(10) Patent No.: US 6,839,583 B1
(45) Date of Patent: Jan. 4, 2005

(54) DISPOSABLE TISSUE PROBE TIP

(75) Inventors: Mark S. Lewandowski, Hutchinson, MN (US); Dean E. Myers, Stewart, MN (US); Joseph P. Ortner, Hutchinson, MN (US); Kenneth R. Quast, Hutchinson, MN (US); Diane L. Rupp, Glencoe, MN (US); Mark A. Schmidt, Darwin, MN (US)

(73) Assignee: Hutchinson Technology Corporation, Hutchinson, MN (US)

( * ) Notice: Subject to any disclaimer, the term of this patent is extended or adjusted under 35 U.S.C. 154(b) by 260 days.

(21) Appl. No.: 09/584,862

(22) Filed: Jun. 1, 2000

Related U.S. Application Data
(60) Provisional application No. 60/137,383, filed on Jun. 3, 1999, provisional application No. 60/137,390, filed on Jun. 3, 1999, and provisional application No. 60/137,382, filed on Jun. 3, 1999.

(51) Int. Cl.[7] .............................................. A61B 5/00
(52) U.S. Cl. ..................................................... 600/344
(58) Field of Search ................................. 600/310, 323, 600/344, 322

(56) References Cited

U.S. PATENT DOCUMENTS

| 4,274,418 A | 6/1981 | Vesterager et al. |
| 4,488,557 A | 12/1984 | Engel |
| 4,515,165 A | 5/1985 | Carroll |
| 4,657,022 A | 4/1987 | Holscher |
| 4,830,014 A | 5/1989 | Goodman et al. |
| 4,899,753 A | 2/1990 | Inoue et al. |
| 4,926,867 A | 5/1990 | Kanda et al. |
| 5,054,488 A | 10/1991 | Muz |
| 5,437,275 A * | 8/1995 | Amundsen et al. .......... 600/323 |
| 5,879,373 A * | 3/1999 | Roper et al. ................. 600/322 |
| 6,144,868 A * | 11/2000 | Parker .......................... 600/310 |
| 6,381,489 B1 | 4/2002 | Ashibe |

FOREIGN PATENT DOCUMENTS

| EP | 0 573 137 | 12/1993 |
| GB | 2 269 012 | 1/1994 |

* cited by examiner

Primary Examiner—Eric F. Winakur
Assistant Examiner—David J. McCrosky
(74) Attorney, Agent, or Firm—Faegre & Benson LLP

(57) ABSTRACT

A disposable tip adapted for use in connection with an optical probe of an instrument. The tip includes a one-piece molded elastomeric base member having a boot and an opaque tissue-engaging surface. The boot releasably mates with and provides an interference/friction fit to the probe. The tissue-engaging surface surrounds and extends from the boot. A window in the base member extends into the boot to transmit light between the probe and tissue. A layer of optically transparent material covers the window on the tissue-engaging surface. Adhesive on the tissue-engaging surface of the base member releasably secures the probe to the tissue being analyzed.

14 Claims, 7 Drawing Sheets

DISPOSABLE TISSUE PROBE TIP

REFERENCE TO RELATED APPLICATIONS

1. This application claims the benefit of the following U.S. Provisional Applications:
   i) Ser. No. 60/137,383 filed on Jun. 3, 1999 and entitled "Disposable Tissue Probe Tip;"
   ii) Ser. No. 60/137,390 filed on Jun. 3, 1999 and entitled "Fiber Optic Light Mixer" and
   iii) Ser. No. 60/137,382 filed on Jun. 3, 1999 and entitled "Calibration Mode Recognition And Calibration Algorithm For Spectrophotometric Instrument."
2. Reference is hereby made to the following commonly assigned U.S. Applications which are incorporated herein by reference:
   i) Ser. No. 09/585,144 filed on Jun. 1, 2000 and entitled "Fiber Optic Light Mixer."
   ii) Ser. No. 09/584,990 filed on Jun. 1, 2000 and entitled "Calibration Mode Recognition And Calibration Algorithm For Spectrophotometric Instrument."

FIELD OF THE INVENTION

The present invention is a disposable tip which can be releasably mounted to the tissue interface probe of an instrument. In particular, the invention is a disposable tip for use with an optical probe of a spectrophotometric-type instrument.

BACKGROUND OF THE INVENTION

Spectrophotometric-type instruments are known and used in a variety of applications. An instrument of this type and an associated patient interface optical probe are, for example, disclosed in the Anderson et al. U.S. Pat. No. 5,879,294. The probe includes a housing and a number of optical fibers. The optical fibers terminate at a tissue-facing surface of the probe and are coupled between the probe and instrument within a cable housing. The embodiment of the probe shown in the Anderson et al. Patent has several send fibers through which light of different wavelengths is transmitted from the instrument to the probe. The tissue-facing surface of the probe is positioned in contact with the tissue being analyzed to transmit the light from the send fibers into the tissue. The receive fiber collects light that has traveled through the tissue being analyzed and transmits the collected light back to the instrument for processing.

There remains a continuing need for improved optical probes for use with spectrophotometric instruments. To provide accurate measurements it is important for the probe to maximize the coupling of the measurement light between the optical fibers and the tissue. In particular, it is important to maximize the coupling of the light emitted from the ends of the send fibers into the tissue, and to maximize the coupling of the collected light back to the receive fibers. Measurement accuracy can also be enhanced by minimizing the amount of ambient light that enters the receive fibers. The probe should be capable of providing a high degree of hygiene. A probe which provides these features and which is efficient to manufacture and convenient to use would be especially desirable.

SUMMARY OF THE INVENTION

The present invention is a disposable tip adapted for use in connection with an optical probe of a medical instrument. The probe tip includes an elastomeric base member having an extended patient tissue-engaging surface and structure for releasably engaging the probe of the medical instrument. A window in the base member transmits light between the probe and the tissue being analyzed. Adhesive on the tissue-engaging surface of the base member releasably secures the tip to a patient. The tip provides a high degree of light coupling between the probe and tissue being analyzed, while at the same time providing a high degree of ambient light exclusion. It can be conveniently attached to and removed from the probe. Since it can be efficiently manufactured and disposed of after a single use, the probe tip also provides a high degree of patient hygiene.

DETAILED DESCRIPTION OF THE PREFERRED EMBODIMENTS

Figure 1:
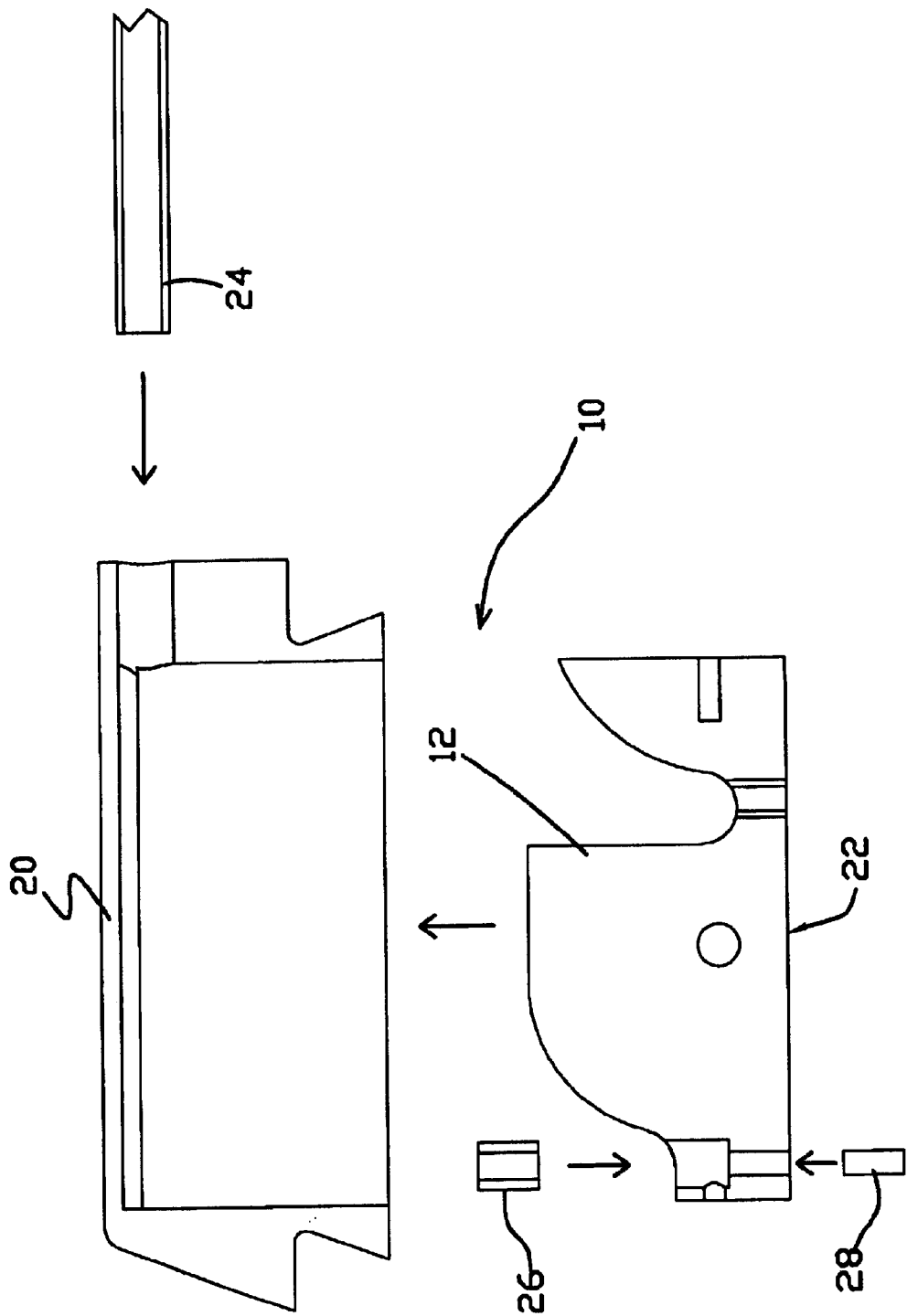
FIG. 1 is an exploded sectional side view of an embodiment of an optical probe to which the disposable tip of the present invention can be releasably attached.
Figure 2:
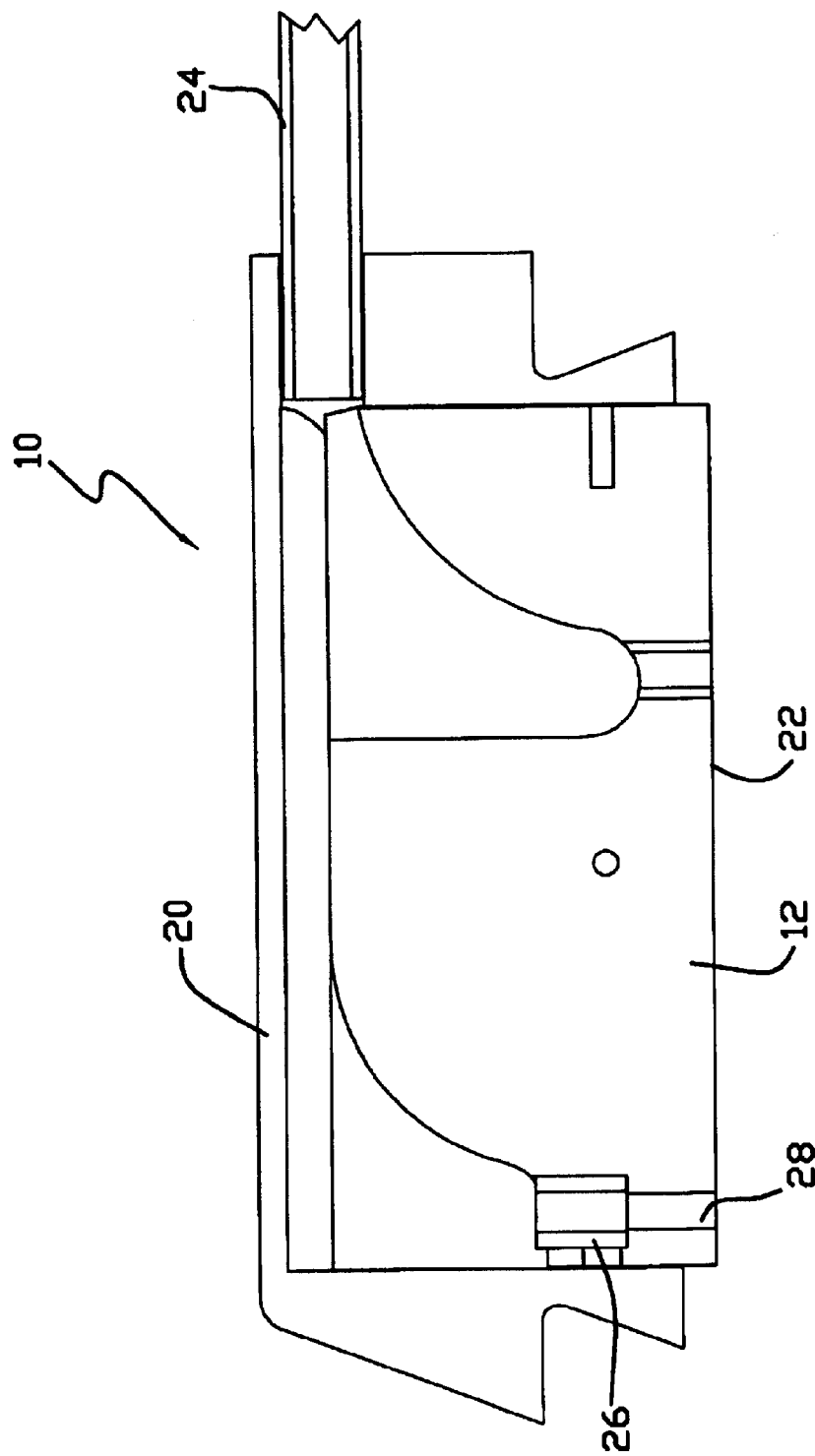
FIG. 2 is a sectional side view of the probe shown in FIG. 1 without the optical fibers.
Figure 3:
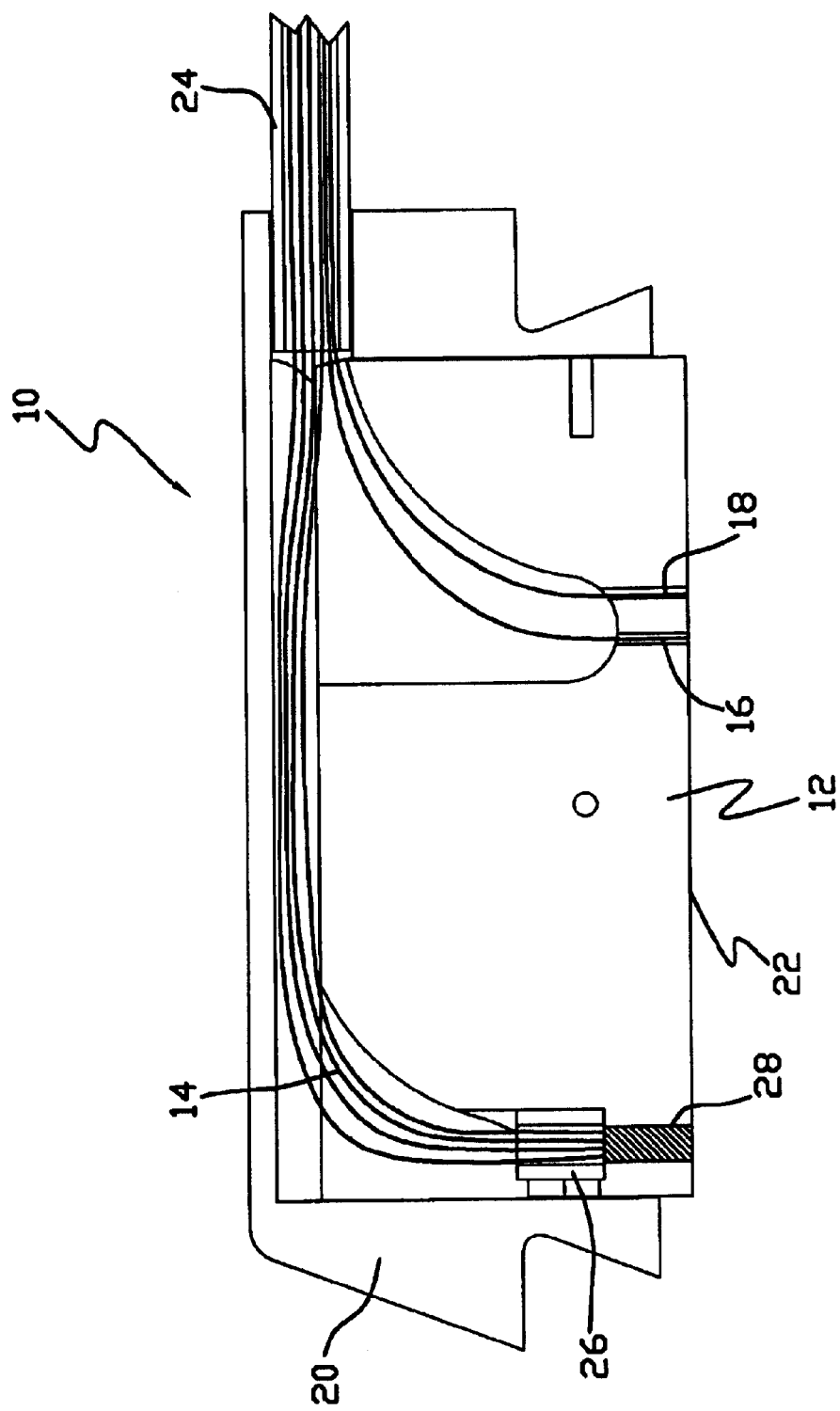
FIG. 3 is a sectional side view of the probe shown in FIG. 1 with the optical fibers.

FIGS. 1–4 illustrate one embodiment of an optical probe 10 and a disposable tip 100 which can be releasably attached to the probe. As shown, the probe 10 includes an insert 12 for holding optical fibers 14, 16 and 18, and a housing 20 into which the insert is mounted. The optical fibers 14, 16 and 18 terminate at a tissue-facing surface 22 of the insert 12 and are coupled between the insert 12 and instrument (not shown) within a cable housing 24. The illustrated embodiment of the invention includes four send fibers 14 through which light of different wavelengths is transmitted to the probe 10. The ends of the send fibers 14 are sealed in a ferrule 26. A mixer fiber 28 is located between the ferrule 26 and the tissue-facing surface 22 of the probe 10. The different wavelengths of light emitted from the ends of the send fibers 14 are mixed within the mixer fiber 28 and thereby scattered throughout the surface area of the mixer fiber at the tissue-facing surface 22. Each wavelength of light will therefore travel through a similar volume of tissue after being transmitted from the probe 10. The ferrule 26 and mixer fiber 28 are described in greater detail in the above-identified related application entitled "Fiber Optic Light Mixer." The receive fiber 18 and calibration recognition fiber 16 also have ends which terminate at the tissue-facing surface 22 of the probe 10. The receive fiber 18 collects light that has traveled through the tissue being analyzed and transmits the collected light to the instrument for processing. Light emitted by the calibration recognition fiber and collected by the receive fiber is used by the instrument to control a calibration procedure in a manner described in the above-identified related application entitled "Calibration Mode Recognition And Calibration Algorithm For Spectrophotometric Instrument."

Figure 4:
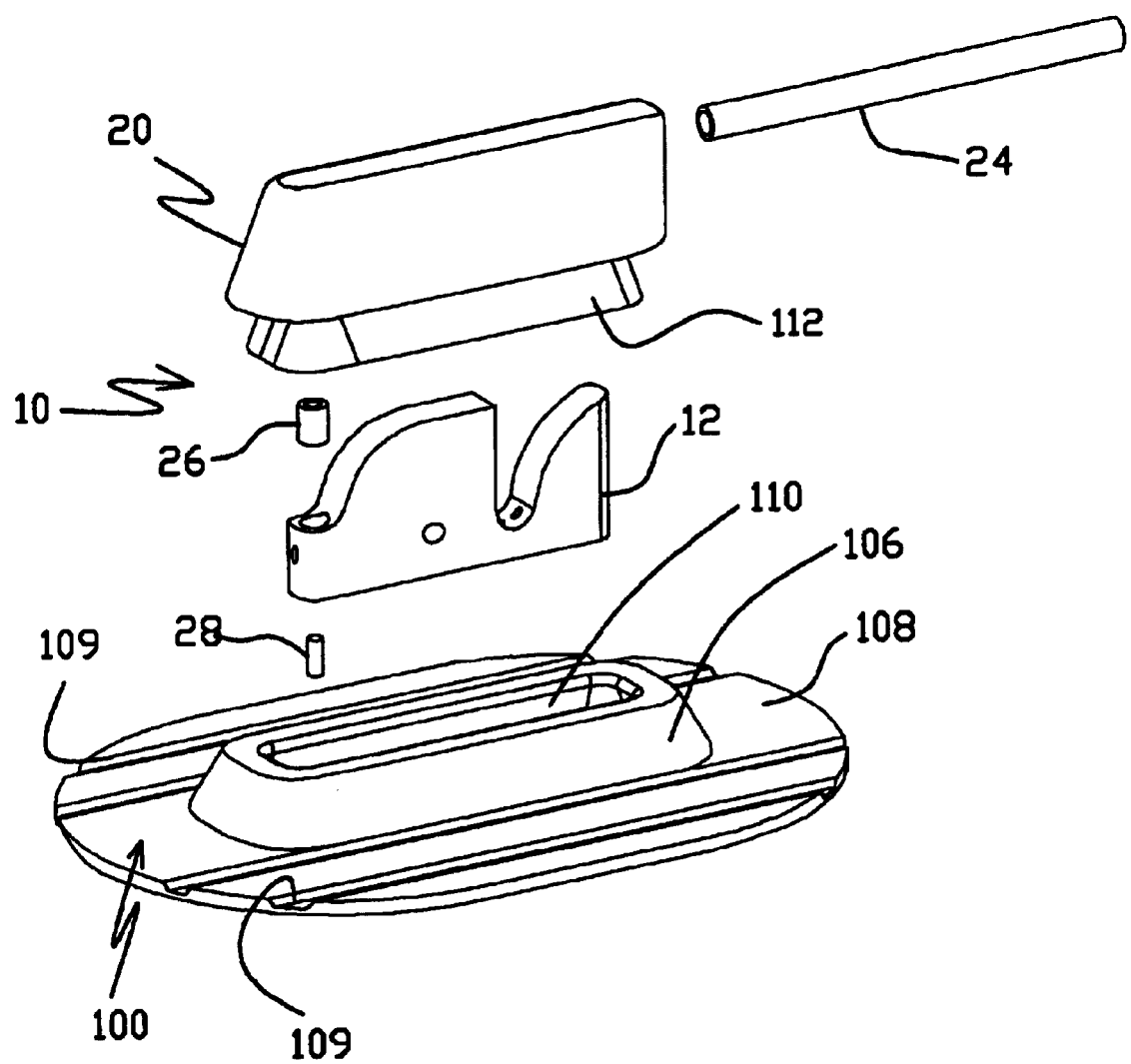
FIG. 4 is an exploded isometric view of the probe shown in FIG. 1 and the disposable tip of the present invention showing the upper surfaces of the components.
Figure 5:
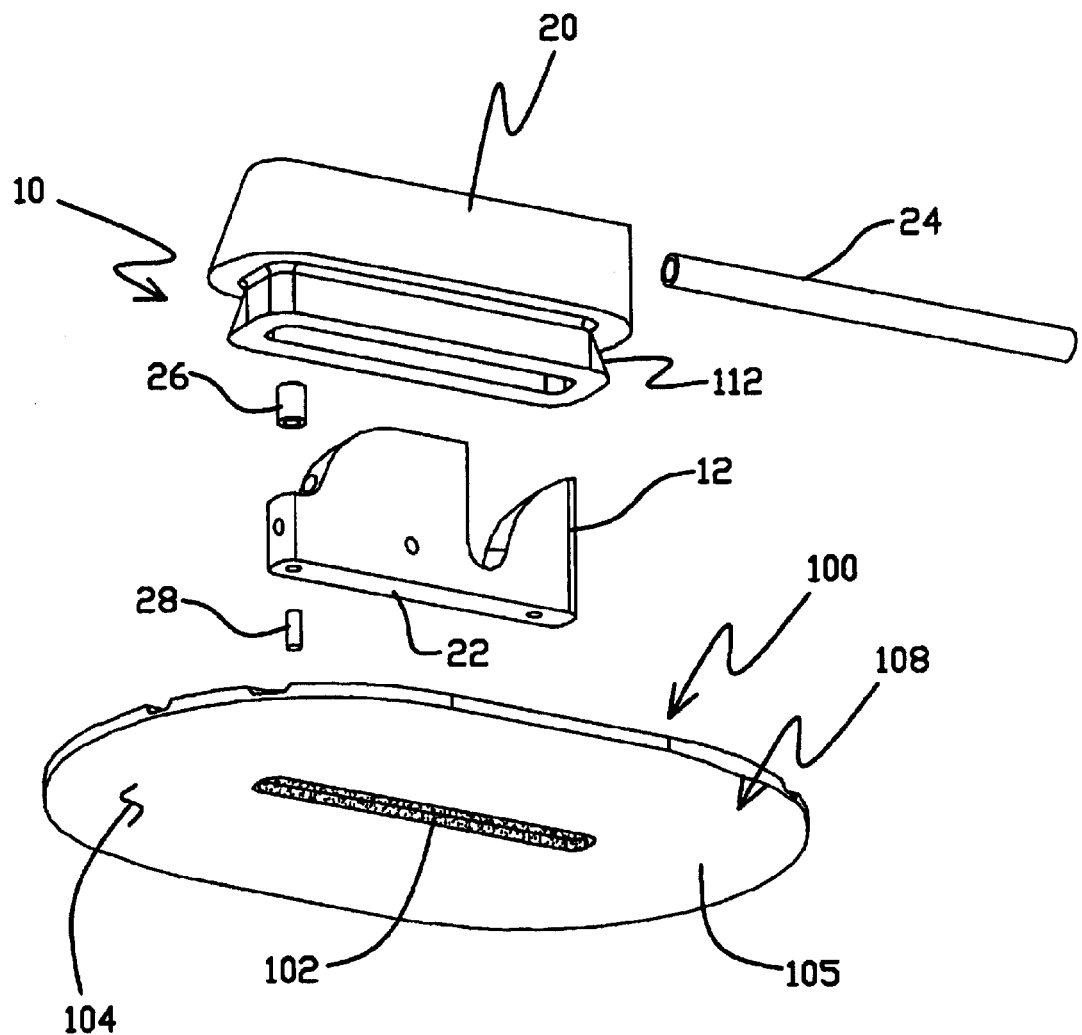
FIG. 5 is a an exploded isometric view of the probe shown in FIG. 1 and the disposable tip of the present invention showing the lower surfaces of the components.
Figure 6:
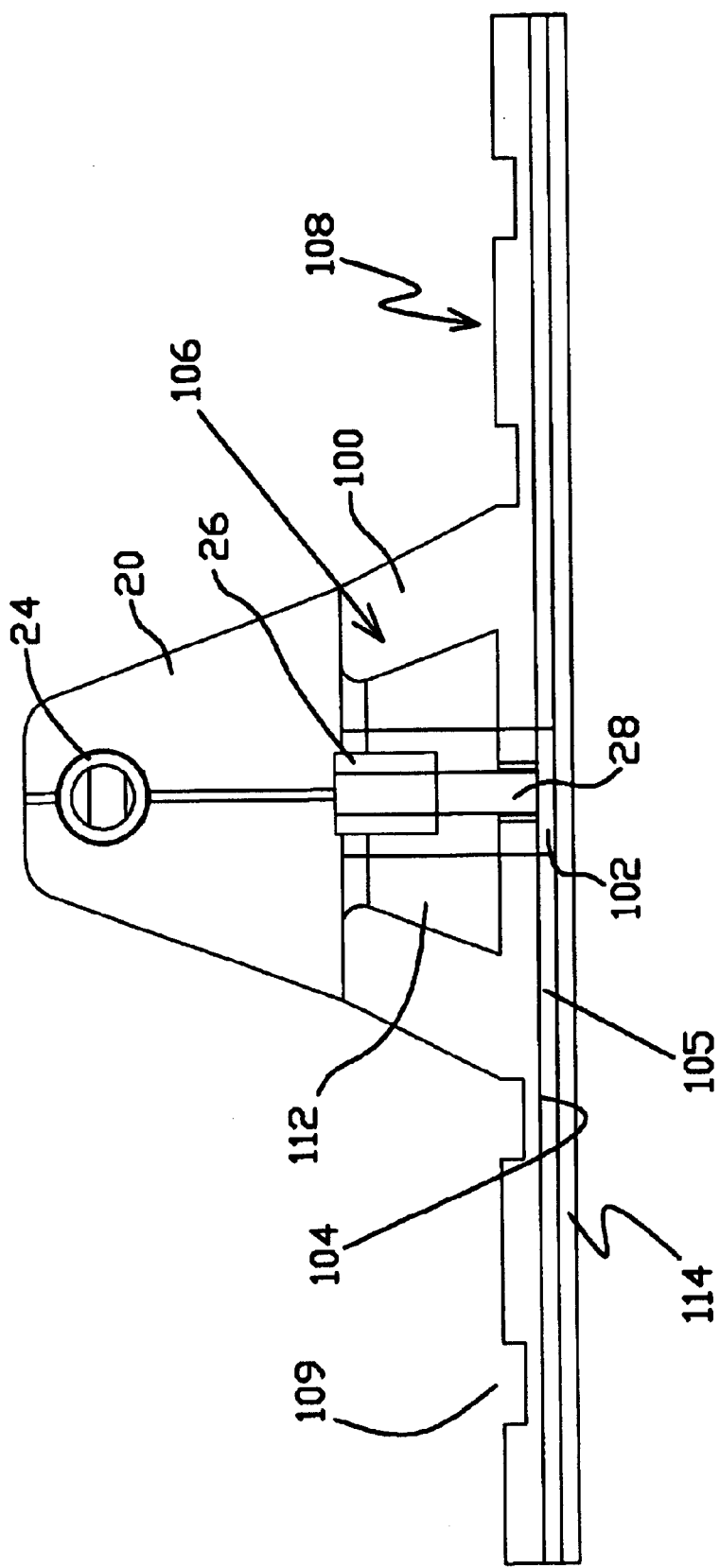
FIG. 6 is a sectional end view of the probe and disposable tip shown in FIGS. 4 and 5.

The disposable tip 100 and the manner by which it is releasably mounted to the probe 10 can be described generally with reference to FIGS. 4–6. The probe tip 100 is an elastomeric fixturing device which is used to removably attach the optical probe 10 to a patient's tissue measurement site (e.g., the skin of a patient). The illustrated embodiment of the tip 100 includes a boot or mating section 106 and a tissue-engaging section 108 which extends from the mating section. The tip 100 can be formed from a 1-piece elastomeric base member molded from flexible material such as silicone rubber (e.g., 50 shore A durometer from Applied Silicone) or polyethylene foam (e.g., Plastasote from Zotefoams Limited). Other suitable materials include isoprene/EPDM/nitrile rubbers, PVC, polyurethane, rubber alloys and vinyl acetate foams. An optically clear window 102 (i.e., a window which transmits the light wavelengths of interest) extends from the mating section 106 through the tissue-engaging section 108 and separates the probe 10 from the patient's skin, thereby functioning as a fluid/infection barrier. A pressure sensitive adhesive 105 on the bottom of tissue-engaging surface of the section 108 holds the tip 100 and attached probe 10 to the measurement site. Once removed from the patient's skin, the tip 100 can be removed from the probe 10 and disposed. Alternatively, the adhesive 105 can be replaced and the tip 100 reused. The materials from which the tip 100 is manufactured are preferably compatible with sterilization processes such as gamma ray and ethylene oxide. Tip 100 can be sterilized by these or other suitable approaches if appropriate for the intended application.

A probe-engaging recess 110 in the mating section 106 is adapted to releasably secure the tip 100 to the probe 10. The illustrated embodiment of the tip 100 has a mating section 106 with a tapered cavity recess 110 which mates and fits snugly to the correspondingly tapered exterior surface of the tip housing 20. In particular, the housing 20 has a tip-engaging section 112 with an outer surface that extends outwardly with increasing distance toward the tissue-facing surface 22. Similarly, the inner surface of the recess 110 extends outwardly with increasing distance toward the tissue-engaging surface 104. The mating configuration of the tip recess 110 and probe section 112 enables the optical probe 10 to be conveniently inserted into and removed from the tip 100 without having to remove the tip from the patient, while at the same time providing a secure attachment between the probe and tip. Furthermore, the sloping surfaces of the mating section 106 and the recess 110 cooperate to urge the tissue-facing surface 22 of the probe 10 toward the tip 100 and the tissue of the patient to which the probe is mounted. In other embodiments of the tip (not shown) the probe and tip are configured with the tissue-facing surface of the probe extending slightly through the window 102 to further initiate intimate contact with the tissue being analyzed. Performance of the probe 10 can be optimized by configuring tip 100, housing 20 and insert 12 in such a manner that the tissue-facing surface 22 at which the optical fibers 16, 18, 28 terminate are positioned as close as possible to the window 102 and the patient's tissue to provide good optical coupling of the send and receive light signals.

In one embodiment the material of the tip 100 is optically opaque and has mating surfaces which overlap the reusable probe tip in a manner to trap ambient light. The tip preferably prevents or minimizes the amount of ambient light entering the tissue being measured near the measurement site. This property is accomplished by the tissue-engaging surface of the section 108 extending from and surrounding the window 102 The fixture can be molded with a saddle or other shape which enables it to conform to the curvature of the leg, arm or other anatomy of the patient. The recessed channels 109 in the upper surface (i.e., the surface opposite the tissue-engaging surface 104) of the section 108 enhance the flexibility of the tip 100 and its ability to conform to the contour of the patient's anatomy to which the tip is mounted.

A double-sided pressure sensitive adhesive 105 can be bonded to the tissue-engaging surface 104 of the tip 100. Alternatively, the adhesive 105 can be a transfer tape (unsupported pressure sensitive adhesive). A single coated tape (pressure sensitive adhesive on the tissue-engaging side only) could also be used. The adhesive and any associated support substrates should be optically clear if they are also functioning as the window 102. Alternatively, a separate section of optically clear material which does not have adhesive properties can be mounted to the tip 100 to function as the window 102. Such a window 102 component can be fixtured within the cavity of the tip 100. For example, the window can be a thin (e.g., about 5 ml), thermoformed transparent (i.e., polyester, polyethylene or polycarbonate) plastic material molded to conform to the hole through the elastomeric tip 100. The window 102 can then be permanently mounted by adhesive to the elastomeric member forming the tip 100. One embodiment of the invention includes a window 102 formed from polyester film (e.g., Mylar Type D from DuPont of Wilmington, Del.). When adapted for use on patients, the adhesive 105 is preferably non-irritating, non-toxic and biocompatible. In one embodiment of the invention, type 1524 double coated tape from 3M Healthcare of St. Paul, Minn., is used for adhesive 105.

A release liner 114 can be used to protect the adhesive 105 and window 102 while the tip is being stored prior to use. The liner 114 should be designed to be easily pulled off the tip 100 to expose the pressure sensitive adhesive 105. The release liner 114 can also be formed from optically clear materials, thereby allowing the tip 100 to be used intermittently on a patient before the release liner 114 is removed and the tip 100 is fixedly mounted to the patient for continuous measurements. Alternatively, a non-transparent paper or plastic release liner 114 can be used if the adhesive component is not designed to provide the window 102 between the tip 100 and probe 10. In yet another embodiment of the invention the adhesive can be applied to the tissue-engaging surface 104 of the tip 100 immediately prior to its use on a patient.

Structural approaches other than the elastomeric interference fit described above can be used to releasably secure the tip 100 to the optical probe 10. For example, snap-type or other buttons or latch mechanisms can be used for this purpose.

The probe tip 100 does not permanently fixture the optical components (e.g., optical fibers 14, 16 and 18 and light mixer 28) of the probe 10 within a "patient sensor." Instead, the optical (and relatively expensive and functionally reusable) components can be removed from the patient without affecting the attachment of the tip 100 to the patient. This reversibility of the connection between the probe 10 and the patient allows the probe to be disconnected and reused on the same patient without having to issue a new disposable tip 100. In situations where a patient is temporarily removed from the instrument (e.g., for x-ray or surgery), the tip 100 can remain attached to the patient and measurement later resumed. The tip 100 can be relatively easily yet securely attached to the housing 20 without the need for hooks, snaps or other fasteners. The tip is also soft and comfortable, resulting in little if any damage to the tissue to which it is mounted.

Figure 7:
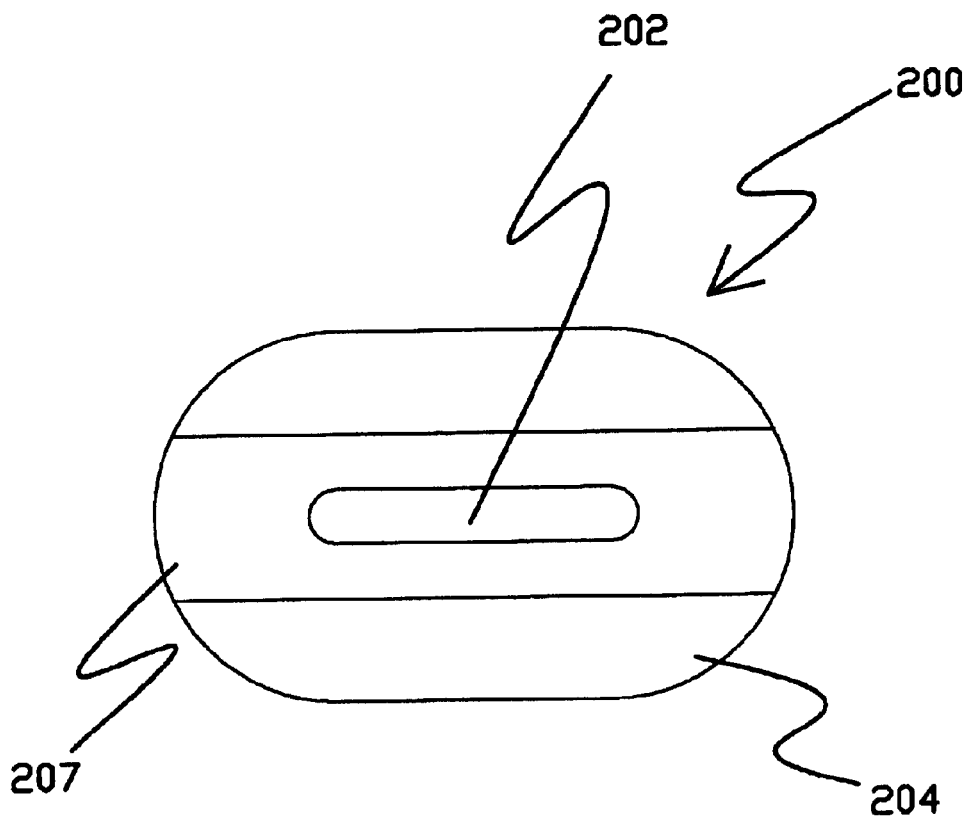
FIG. 7 is a bottom view of a second embodiment of a tip in accordance with the present invention.

FIG. 7 is an illustration of the bottom of a tip 200 in accordance with another embodiment of the invention. Tip 200 can be formed from two overlaying sheets of polyethylene foam (not separately visible in FIG. 7) and a sheet of double sided adhesive having a release liner (also not shown in FIG. 7) by thermal compression molding processes in a steel rule die. The bottom polyethylene layer (i.e., the layer with the tissue-engaging surface 204) is preferably black or otherwise optically opaque to the sensitive wavelength range of the spectrophotometric instrument to minimize the effects of ambient light on the measurement, while the top layer can be colored to enable printing and/or to indicate the size of the tip 200. The molded sheets can be large enough to include a plurality of adjacent tips having their windows 202 aligned with one another and cut from the sheets during the molding operation. Following the molding operation the release liner can be removed and a strip 207 of optically clear polyester (e.g., Mylar Type D from DuPont) or other material applied to the adhesive across all the windows 202. The release liner can then be reapplied, and the individual tips 200 cut from the molded sheet. Tips 200 manufactured using this method will have the strip 207 of the clear material covering the window 202 extending between opposite ends of the tips, yet leaving sufficient exposed adhesive to enable the tip to securely adhere to the patient. A strip 207 of this type, as opposed to a piece of optically clear material over the window but surrounded by adhesive, allows moisture to relatively easily diffuse from the tissue/window interface.

Although the present invention has been described with reference to preferred embodiments, those skilled in the art will recognize that changes can be made in form and detail without departing from the spirit and scope of the invention.

What is claimed is:

1. A disposable tip adapted for use in connection with an optical probe of an instrument, including:
    a one piece elastomeric base member having an extended tissue-engaging surface and structure for releasably engaging the optical probe of the instrument, the structure for releasably engaging includes a cavity for engaging a projection on the probe, the cavity having outwardly sloping inner walls with increasing distance toward the tissue-facing surface for mating with the projection on the probe; and
    a window in the base member for transmitting light between the probe and a tissue.

2. The tip of claim 1 and further including adhesive on the tissue-enganging surface of the base member for releaseably securing the tip to a patient.

3. The tip of claim 2 and further including a release liner covering the adhesive.

4. The tip of claim 1 wherein the cavity surrounds the window.

5. The tip of claim 1 wherein the structure for engaging the optical probe surrounds the window.

6. The tip of claim 1 wherein the window includes an optically transparent member mounted to the base member.

7. The tip of claim 1 and further including adhesive on an optically clear substrate which covers the window and tissue-engaging surface of the base member.

8. The tip of claim 1 wherein the tip and window are a one-piece member.

9. The tip of claim 1 wherein the structure for releasably engaging the probe provides an interference/friction fit to the probe.

10. The tip of claim 1 wherein the tissue-engaging surface of the base member is optically opaque.

11. A disposable tip adapted for use in connection with an optical probe of an instrument, including:
    a one-piece molded elastomeric base member including:
        a boot having a cavity with outwardly sloping interior walls with increasing distance toward the tissue-facing surface for releasably mating with and providing an interference/friction fit to the probe; and
        a tissue-engaging surface surrounding and extending from the boot;
    a window in the base member extending into the cavity of the boot, for transmitting light between the probe and tissue;
    a layer of optically transparent material over the window on the tissue-engaging surface; and
    adhesive on the tissue-engaging surface of the base member, for releasably securing the probe to tissue being analyzed.

12. The disposable tip of claim 11 wherein the tissue-engaging surface is optically opaque.

13. The disposable tip of claim 12 and further including a release liner covering the adhesive.

14. The disposable tip of claim 11 wherein at least a portion of the optically transparent window extends to an edge of the base member.

* * * * *